US012778682B2

(12) United States Patent
Wolfsberger

(10) Patent No.: US 12,778,682 B2
(45) Date of Patent: *Nov. 3, 2026

(54) ORAL PATIENT TRACKING DEVICE AND METHOD OF USING THE SAME

(71) Applicant: Medtronic Navigation, Inc., Lafayette, CO (US)

(72) Inventor: Stefan Wolfsberger, Vienna (AT)

(73) Assignee: Medtronic Navigation, Inc., Lafayette, CO (US)

( * ) Notice: Subject to any disclaimer, the term of this patent is extended or adjusted under 35 U.S.C. 154(b) by 43 days.

This patent is subject to a terminal disclaimer.

(21) Appl. No.: 18/750,782

(22) Filed: Jun. 21, 2024

(65) Prior Publication Data

US 2024/0341865 A1 Oct. 17, 2024

Related U.S. Application Data

(60) Continuation of application No. 18/089,527, filed on Dec. 27, 2022, now Pat. No. 12,016,643, which is a (Continued)

(51) Int. Cl.
*A61B 34/20* (2016.01)
*A61B 1/233* (2006.01)
(Continued)

(52) U.S. Cl.
CPC .............. *A61B 34/20* (2016.02); *A61B 1/233* (2013.01); *A61B 90/361* (2016.02); *A61B 1/24* (2013.01);
(Continued)

(58) Field of Classification Search
CPC ........... A61B 1/233; A61B 1/24; A61B 17/24; A61B 2017/00221; A61B 2017/00477; A61B 2017/00526; A61B 2017/00898; A61B 2034/2051; A61B 2034/2055; A61B 2034/2072; A61B 2090/3762; A61B 2090/3983; A61B 34/20; A61B 34/30; A61B 5/061; A61B 5/1114; A61B 5/6819; A61B 5/682; A61B 90/361; B33Y 80/00
See application file for complete search history.

(56) References Cited

U.S. PATENT DOCUMENTS 5,592,939 A 1/1997 Martinelli
5,913,820 A 6/1999 Bladen et al.
(Continued)

FOREIGN PATENT DOCUMENTS

| | | |
|---|---|---|
| EP | 1523951 | 4/2005 |
| EP | 2311401 A1 | 4/2011 |
| WO | 2018115576 A1 | 6/2018 |

OTHER PUBLICATIONS

International Preliminary Report on Patentability mailed Nov. 11, 2021 in corresponding/related International Application No. PCT/US2020/030757.

(Continued)

*Primary Examiner* — Michael T Rozanski
(74) *Attorney, Agent, or Firm* — Mueting Raasch Group

(57) ABSTRACT

A patient tracking device for insertion into an oral cavity includes a sensor housing comprising a first surface shaped to correspond to a pallet within the oral cavity. At least a portion of the first surface affixes the sensor housing to the oral cavity. An electromagnetic sensor is coupled to the sensor housing.

19 Claims, 12 Drawing Sheets

Related U.S. Application Data division of application No. 16/401,456, filed on May 2, 2019, now Pat. No. 11,547,491.

(51) Int. Cl.

| | |
|---|---|
| ***A61B 1/24*** | (2006.01) |
| ***A61B 5/06*** | (2006.01) |
| ***A61B 34/30*** | (2016.01) |
| ***A61B 90/00*** | (2016.01) |

(52) U.S. Cl.

CPC ....... *A61B 5/061* (2013.01); *A61B 2034/2055* (2016.02); *A61B 34/30* (2016.02); *A61B 2090/3983* (2016.02)

(56) References Cited

U.S. PATENT DOCUMENTS

| | | | |
|---|---|---|---|
| 5,983,126 | A | 11/1999 | Wittkampf |
| 6,445,943 | B1 | 9/2002 | Ferre et al. |
| 6,474,341 | B1 | 11/2002 | Hunter et al. |
| 6,687,531 | B1 | 2/2004 | Ferre et al. |
| 6,738,656 | B1 | 5/2004 | Ferre et al. |
| 6,855,740 | B2 | 2/2005 | Siegel |
| 6,940,941 | B2 | 9/2005 | Gregerson et al. |
| 7,001,045 | B2 | 2/2006 | Gregerson et al. |
| 7,106,825 | B2 | 9/2006 | Gregerson et al. |
| 7,108,421 | B2 | 9/2006 | Gregerson et al. |
| 7,188,998 | B2 | 3/2007 | Gregerson et al. |
| 7,691,079 | B2 | 4/2010 | Gobel |
| 7,751,865 | B2 | 7/2010 | Jascob et al. |
| 8,644,907 | B2 | 2/2014 | Hartmann et al. |
| 8,702,626 | B1 | 4/2014 | Kim et al. |
| 9,167,961 | B2 | 10/2015 | Makower et al. |
| 9,241,657 | B2 | 1/2016 | Vollmer et al. |
| 11,446,094 | B2 | 9/2022 | Wolfsberger |
| 11,547,491 | B2 | 1/2023 | Wolfsberger |
| 2004/0030243 | A1 | 2/2004 | Warschewske et al. |
| 2005/0085715 | A1 | 4/2005 | Dukesherer et al. |
| 2005/0168396 | A1 | 8/2005 | Victorian et al. |
| 2011/0092803 | A1 | 4/2011 | Hynes et al. |
| 2012/0256750 | A1 | 10/2012 | Novak |
| 2013/0102893 | A1 | 4/2013 | Vollmer et al. |
| 2013/0331686 | A1 | 12/2013 | Freysinger et al. |
| 2014/0135868 | A1 | 5/2014 | Bashyam |
| 2014/0275698 | A1 | 9/2014 | Lidstrom et al. |
| 2014/0275707 | A1 | 9/2014 | Lidstrom et al. |
| 2014/0343395 | A1 | 11/2014 | Choi et al. |
| 2015/0146901 | A1 | 5/2015 | Richardson et al. |
| 2015/0209228 | A1 | 7/2015 | Bruce et al. |
| 2015/0320982 | A1 | 11/2015 | Massicotte |
| 2015/0374443 | A1 | 12/2015 | Mittauer et al. |
| 2017/0202480 | A1 | 7/2017 | Kim et al. |
| 2018/0263725 | A1 | 9/2018 | Pesach et al. |
| 2020/0345424 | A1 | 11/2020 | Wolfsberger |
| 2020/0345425 | A1 | 11/2020 | Wolfsberger |

OTHER PUBLICATIONS

International Preliminary Report on Patentability mailed Nov. 11, 2021, in corresponding/related International Application No. PCT/US2020/030733.

International Search Report and Written Opinion mailed Jul. 23, 2020 in corresponding/related International Application No. PCT/US2020/030733.

International Search Report and Written Opinion mailed Jul. 29, 2020 in corresponding/related International Application No. PCT/US2020/030757.

Jackman et al: "Nasal Packing—an overview—ScienceDirect Topics Complications of Nasal Surgery and Epistaxis Management", Complications in Head and Neck Surgery, Jan. 1, 2009, XP055715556, Retrieved from the Internet: URL:https://www.sciencedirect.com/topics/medicine-and-dentistry/nasal-packing [retrieved on Jul. 16, 2020].

U.S. Appl. No. 18/089,527, filed Dec. 27, 2022, Stefan Wolfsberger.

U.S. Appl. No. 16/401,456, filed May 2, 2019, Stefan Wolfsberger.

U.S. Appl. No. 17/901,987, filed Sep. 2, 2022, Stefan Wolfsberger.

U.S. Appl. No. 16/401,412, filed May 2, 2019, Stefan Wolfsberger.

PCT/US2020/030733, Apr. 30, 2020, Stefan Wolfsberger.

PCT/US2020/030757, Apr. 30, 2020, Stefan Wolfsberger.

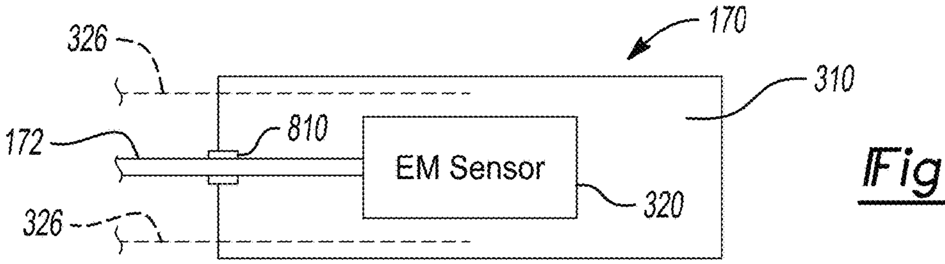
Fig-8A
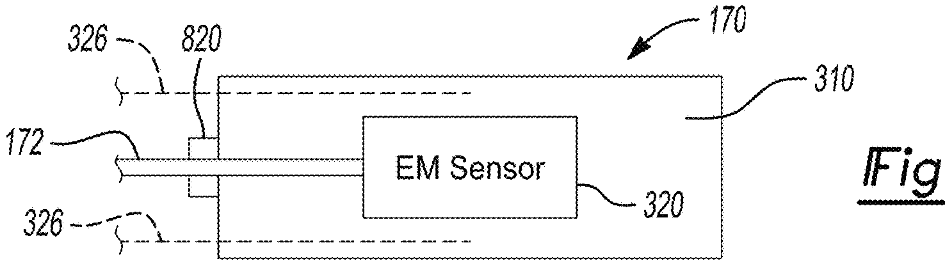
Fig-8B
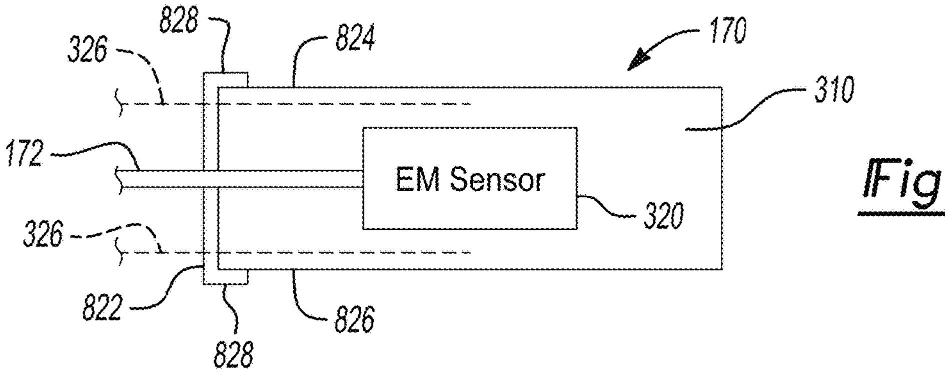
Fig-8C
Fig-9A
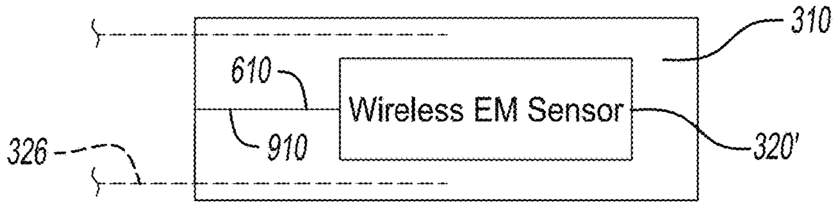
Fig-9B
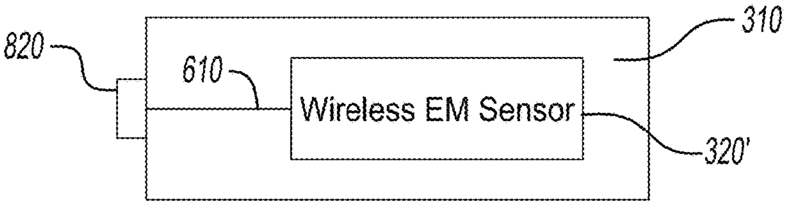
Fig-9C
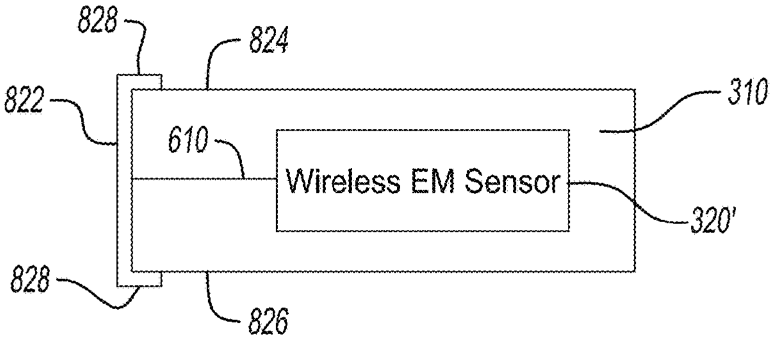

ORAL PATIENT TRACKING DEVICE AND METHOD OF USING THE SAME

CROSS-REFERENCE TO RELATED APPLICATIONS

This application is a continuation of U.S. patent application Ser. No. 18/089,527 filed Dec. 27, 2022, which is divisional of U.S. patent application Ser. No. 16/401,456 filed May 2, 2019, now U.S. Pat. No. 11,547,491 issued Jan. 10, 2023. The entire disclosure of the above applications are incorporated herein by reference.

This application includes subject matter related to U.S. patent application Ser. No. 17/901,987 filed Sep. 2, 2022 which is continuation of U.S. patent application Ser. No. 16/401,412 filed May 2, 2019, now U.S. Pat. No. 11,446,904 issued Sep. 20, 2022. The entire disclosure of the above applications are incorporated herein by reference.

FIELD

The present disclosure relates to registration between a patient, and image data and particularly to a system to track movement of a patient during a procedure.

BACKGROUND

This section provides background information related to the present disclosure which is not necessarily prior art.

Image guided medical and surgical procedures utilize patient images obtained prior to or during a medical procedure to guide a physician performing the procedure. Recent advances in imaging technology, especially in imaging technologies that produce highly-detailed, two, three, and four dimensional images, such as computed tomography (CT), magnetic resonance imaging (MRI), fluoroscopic imaging (such as with a C-arm device), positron emission tomography (PET), and ultrasound imaging (US) has increased the interest in image guided medical procedures.

Typical image guided navigation systems generally require dynamic reference frames to track the position of the patient should patient movement occur during the assisted procedure. The dynamic reference frame is generally affixed to the patient in an immovable fashion. The dynamic reference frame may also be used as a fiducial marker and may, therefore, be attached to the patient during the acquisition of pre-operative images. This enables the image space to be aligned with patient space during the navigated procedure. For example, with relation to a cranial procedure, the dynamic reference frame can be attached to the skull by a bone screw. For other procedures, the dynamic reference frame may be fixed to other boney portions also with bone screws. Methods for affixing the dynamic reference frames to a patient can be invasive or inaccurate due to movement. Bone affixed dynamic reference frames require an incision that can often be more than two centimeters in length. Skin mobility can lead to undesirable movement when using a non-invasive dynamic reference frame attachment such as tape.

SUMMARY

This section provides a general summary of the disclosure, and is not a comprehensive disclosure of its full scope or all of its features.

In one aspect of the disclosure, a patient tracking device for insertion into a body cavity includes a flexible conformable sensor housing having a sensor cavity therein. The housing conforms to the body cavity when inserted therein. A sensor is disposed within the housing.

In another aspect of the disclosure, a method includes determining a body cavity for receiving a flexible resilient sensor housing; determining a sensor housing corresponding the body cavity; inserting the sensor housing having a sensor within a sensor cavity of the housing into the body cavity; conforming the sensor housing to a shape of the body cavity; collecting position data of the body cavity from the sensor; maintaining registration of an image space to a patient space in response to the position data; and displaying a navigated location.

In yet another aspect of the disclosure, a method of forming a patient tracking device includes forming a sensor cavity within a flexible conformable housing sized to fit within a body cavity; inserting an electromagnetic sensor within the sensor cavity; and retaining the electromagnetic sensor within the sensor cavity.

In still another aspect of the disclosure, a patient tracking device for insertion into an oral cavity includes a sensor housing comprising a first surface shaped to correspond to a pallet within the oral cavity. At least a portion of the first surface affixes the sensor housing to the oral cavity. An electromagnetic sensor is coupled to the sensor housing.

In another aspect of the disclosure, a method includes determining a shape of a pallet of an oral cavity of a patient, forming a sensor housing comprising a first surface based on the shape of the pallet, coupling an electromagnetic sensor to the sensor housing and affixing the sensor housing within the oral cavity.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 8A is a cross-sectional view of an EM sensor within a housing with an adhesive retainer;

FIG. 8B is a cross-sectional view of an EM sensor within a housing with a clip or fastener;

FIG. 8C is a second cross-sectional view of an EM sensor within a housing with a clip or fastener;

FIG. 9A is a side view of the housing 310 having an RF EM sensor and the retainer being adhesive;

FIG. 9B is a side view of the housing 310 having an RF EM sensor and the retainer being a clip or fastener;

FIG. 9C is a second example of a side view of the housing 310 having an RF EM sensor and the retainer being a clip or fastener;

Corresponding reference numerals indicate corresponding parts throughout the several views of the drawings.

DETAILED DESCRIPTION

Example embodiments will now be described more fully with reference to the accompanying drawings.

The subject disclosure is directed to an exemplary embodiment of a surgical procedure on a subject, such as a human patient. It is understood, however, that the system and methods described herein are merely exemplary and not intended to limit the scope of the claims included herein. In various embodiments, it is understood, that the systems and methods may be incorporated into and/or used on non-animate objects. The systems may be used to, for example, to register coordinate systems between two systems for use on manufacturing systems, maintenance systems, and the like. For example, automotive assembly may use one or more robotic systems including individual coordinate systems that may be registered together for coordinated or consorted actions. Accordingly, the exemplary illustration of a surgical procedure herein is not intended to limit the scope of the appended claims. Various embodiments of a patient tracking device are disclosed in U.S. Pat. No. 11,446,094 issued Sep. 20, 2022, incorporated herein by reference.

Figure 1:
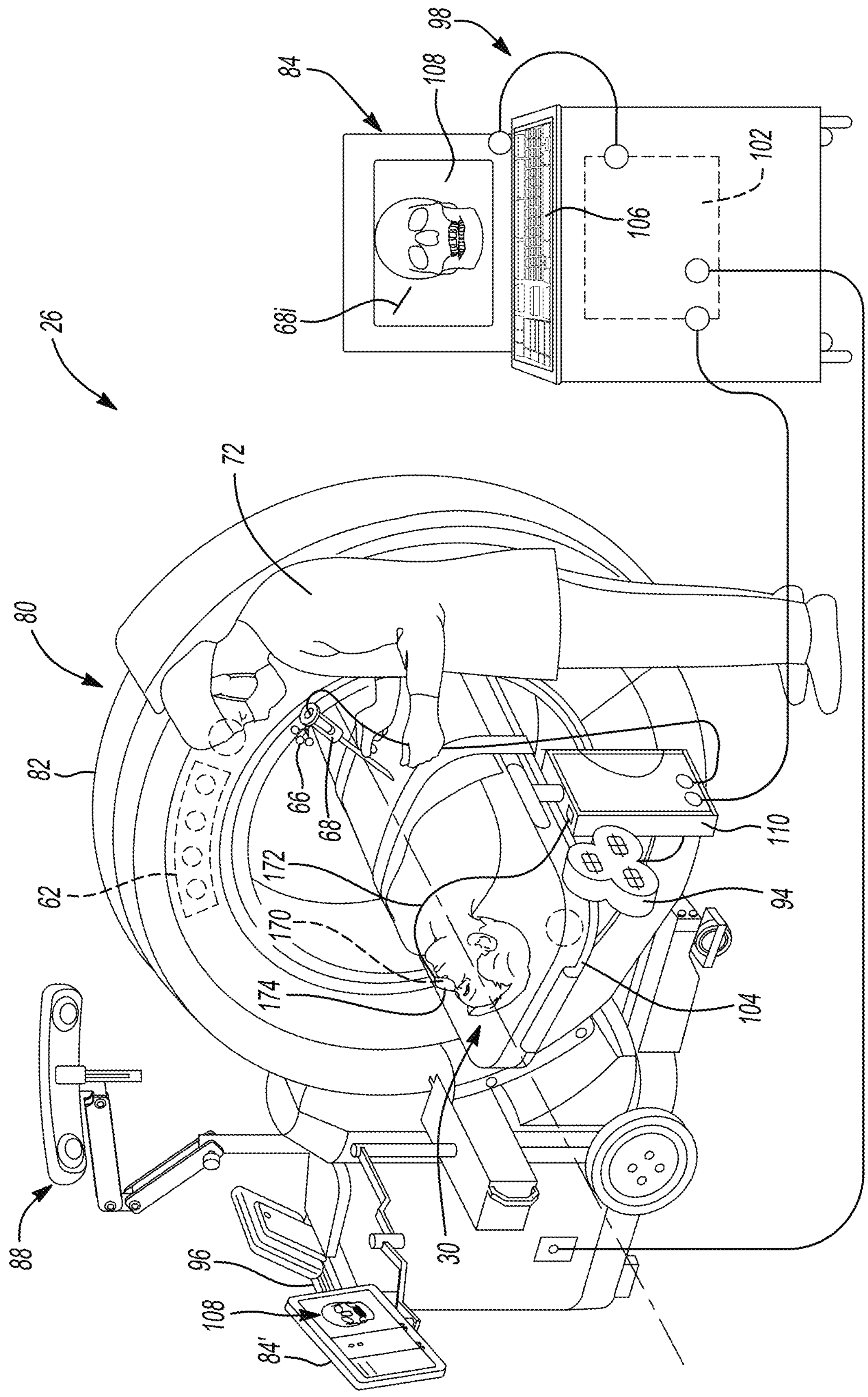
FIG. 1 is an environmental view in an operating theatre that uses a DRF (endonasal or palatal patient tracker) of the present disclosure.

FIG. 1 is a diagrammatic view illustrating an overview of a procedure room or arena. In various embodiments, the procedure room may include a surgical suite having a navigation system 26 that can be used relative to a patient or subject 30. The navigation system 26 can be used to track the location of one or more tracking devices, tracking devices may include an imaging system tracking device 62, and/or a tool tracking device 66. A tool 68 may be any appropriate tool such as a drill, forceps, catheter, speculum or other tool operated by a user 72. The tool 68 may also include an implant, such as a stent, a spinal implant or orthopedic implant. It should further be noted that the navigation system 26 may be used to navigate any type of instrument, implant, stent or delivery system, including: guide wires, arthroscopic systems, orthopedic implants, spinal implants, deep brain stimulation (DBS) probes, etc. Moreover, the instruments may be used to navigate or map any region of the body. The navigation system 26 and the various instruments may be used in any appropriate procedure, such as one that is generally minimally invasive or an open procedure including cranial procedures.

An imaging device 80 may be used to acquire pre-, intra-, or post-operative or real-time image data of a subject, such as the subject 30. It will be understood, however, that any appropriate subject can be imaged and any appropriate procedure may be performed relative to the subject. In the example shown, the imaging device 80 comprises an O-Arm® imaging device sold by Medtronic Navigation, Inc. having a place of business in Louisville, Colorado, USA. The imaging device 80 may have a generally annular gantry housing 82 in which an image capturing portion is moveably placed. The image capturing portion may include an x-ray source or emission portion and an x-ray receiving or image receiving portion located generally or as practically possible 180 degrees from each other and mounted on a rotor relative to a track or rail. The image capturing portion can be operable to rotate 360 degrees during image acquisition. The image capturing portion may rotate around a central point or axis, allowing image data of the subject 80 to be acquired from multiple directions or in multiple planes. The imaging device 80 can include those disclosed in U.S. Pat. Nos. 7,188,998; 7,108,421; 7,106,825; 7,001,045; and 6,940,941; all of which are incorporated herein by reference, or any appropriate portions thereof. In one example, the imaging device 80 can utilize flat plate technology having a 1,720 by 1,024 pixel viewing area.

The position of the imaging device 80, and/or portions therein such as the image capturing portion, can be precisely known relative to any other portion of the imaging device 80. The imaging device 80, according to various embodiments, can know and recall precise coordinates relative to a fixed or selected coordinate system. This can allow the imaging system 80 to know its position relative to the patient 30 or other references. In addition, as discussed herein, the precise knowledge of the position of the image capturing portion can be used in conjunction with a tracking system to determine the position of the image capturing portion and the image data relative to the tracked subject, such as the patient 30.

The imaging device 80 can also be tracked with a tracking device 62. The image data defining an image space acquired of the patient 30 can, according to various embodiments, be inherently or automatically registered relative to an object space. The object or patient space can be the space defined by a patient 30 in the navigation system 26. The automatic registration can be achieved by including the tracking device 62 on the imaging device 80 and/or the determinable precise location of the image capturing portion. According to various embodiments, as discussed herein, imageable portions, virtual fiducial points and other features can also be used to allow for registration, automatic or otherwise. It will be understood, however, that image data can be acquired of any subject which will define the patient or subject space. Patient space is an exemplary subject space. Registration allows for a translation between patient space and image space.

The patient 80 can also be tracked as the patient moves with an optical tracker 88. Alternatively, or in addition thereto, the patient 30 may be fixed within navigation space defined by the navigation system 26 to allow for registration. As discussed further herein, registration of the image space to the patient space or subject space allows for navigation of the instrument 68 with the image data. When navigating the instrument 68, a position of the instrument 68 can be illustrated relative to image data acquired of the patient 30 on a display device 84. Various tracking systems, such as one including an optical localizer 88 or an electromagnetic (EM) localizer 94 can be used to track the instrument 68.

More than one tracking system can be used to track the instrument 68 in the navigation system 26. According to various embodiments, these can include an electromagnetic tracking (EM) system having the EM localizer 94 and/or an optical tracking system having the optical localizer 88. Either or both of the tracking systems can be used to track selected tracking devices, as discussed herein. It will be understood, unless discussed otherwise, that a tracking device can be a portion trackable with a selected tracking system. A tracking device need not refer to the entire member or structure to which the tracking device is affixed or associated.

It is further appreciated that the imaging device 80 may be an imaging device other than the O-Arm® imaging device and may include in addition or alternatively a fluoroscopic C-arm. Other exemplary imaging devices may include fluoroscopes such as bi-plane fluoroscopic systems, ceiling mounted fluoroscopic systems, cath-lab fluoroscopic systems, fixed C-arm fluoroscopic systems, isocentric C-arm fluoroscopic systems, 3D fluoroscopic systems, etc. Other appropriate imaging devices can also include MRI, CT, ultrasound, etc.

In various embodiments, an imaging device controller 96 may control the imaging device 80 and can receive the image data generated at the image capturing portion and store the images for later use. The controller 96 can also control the rotation of the image capturing portion of the imaging device 80. It will be understood that the controller 96 need not be integral with the gantry housing 82, but may be separate therefrom. For example, the controller may be a portions of the navigation system 26 that may include a processing and/or control system including a processing unit or processing system 102. The controller 96, however, may be integral with the gantry housing 82 and may include a second and separate processor, such as that in a portable computer.

The patient 30 can be fixed onto an operating table 104. According to one example, the table 104 can be an Axis Jackson @ operating table sold by OSI, a subsidiary of Mizuho Ikakogyo Co., Ltd., having a place of business in Tokyo, Japan or Mizuho Orthopedic Systems, Inc. having a place of business in California, USA. Patient positioning devices can be used with the table, and include a Mayfield® clamp or those set forth in commonly assigned U.S. patent application Ser. No. 10/405,068 entitled "An Integrated Electromagnetic Navigation And Patient Positioning Device", filed Apr. 1, 2003 which is hereby incorporated by reference.

The position of the patient 30 relative to the imaging device 80 can be determined by the navigation system 26. The tracking device 62 can be used to track and locate at least a portion of the imaging device 80, for example the gantry housing 82. The patient 30 can be tracked with a non-invasive dynamic reference frame 170, as discussed further herein. That is, a patient tracking device 170 may be used to receive or generate electromagnetic signals that are communicated through a cable 172 to an interface portion 110. As is discussed below wireless communication to the interface portion 110 may also be used. The patient tracking device 170 may also be referred to as a dynamic reference frame. The patient tracking device 170 is located within a substantially rigid body cavity. In the following example, the body cavity is a nasal cavity or palate as will be described in more detail below. A piece of tape 174 may be used to secure the cable 172 to the patient 30.

Accordingly, the position of the patient 30 relative to the imaging device 80 can be determined. Further, the location of the imaging portion can be determined relative to the housing 82 due to its precise position on the rail within the housing 82, substantially inflexible rotor, etc. The imaging device 80 can include an accuracy of within 10 microns, for example, if the imaging device 80 is an O-Arm® imaging device sold by Medtronic Navigation, Inc. having a place of business in Louisville, Colorado. Precise positioning of the imaging portion is further described in U.S. Pat. Nos. 7,188,998; 7,108,421; 7,106,825; 7,001,045; and 6,940,941; all of which are incorporated herein by reference, According to various embodiments, the imaging device 80 can generate and/or emit x-rays from the x-ray source that propagate through the patient 30 and are received by the x-ray imaging receiving portion. The image capturing portion generates image data representing the intensities of the received x-rays. Typically, the image capturing portion can include an image intensifier that first converts the x-rays to visible light and a camera (e.g. a charge couple device) that converts the visible light into digital image data. The image capturing portion may also be a digital device that converts x-rays directly to digital image data for forming images, thus potentially avoiding distortion introduced by first converting to visible light.

Two dimensional and/or three dimensional fluoroscopic image data that may be taken by the imaging device 80 can be captured and stored in the imaging device controller 96. Multiple image data taken by the imaging device 80 may also be captured and assembled to provide a larger view or image of a whole region of a patient 30, as opposed to being directed to only a portion of a region of the patient 30. For example, multiple image data of the patient's 30 spine may be appended together to provide a full view or complete set of image data of the spine.

The image data can then be forwarded from the image device controller 96 to the navigation computer and/or processor system 102 that can be a part of a controller or work station 98 having the display 84 and a user interface 106. It will also be understood that the image data is not necessarily first retained in the controller 96, but may also be directly transmitted to the work station 98. The work station 98 can provide facilities for displaying the image data as an image 108 on the display 84, saving, digitally manipulating, or printing a hard copy image of the received image data. The user interface 106, which may be a keyboard, mouse, touch pen, touch screen or other suitable device, allows the user 72 to provide inputs to control the imaging device 80, via the image device controller 96, or adjust the display settings of the display 84. The work station 98 may also direct the image device controller 96 to adjust the image capturing portion of the imaging device 80 to obtain various two-dimensional images along different planes in order to generate representative two-dimensional and three-dimensional image data.

With continuing reference to FIG. 1, the navigation system 26 can further include the tracking system including either or both of the electromagnetic (EM) localizer 94 and/or the optical localizer 88. The tracking systems may include a controller and interface portion 110. The interface portion 110 can be connected to the processor system 102, which can include a processor included within a computer. The EM tracking system may include the STEALTHSTATION® AXIEM™ Navigation System, sold by Medtronic Navigation, Inc. having a place of business in Louisville, Colorado; or can be the EM tracking system described in U.S. Pat. No. 7,751,865 issued Jul. 6, 2010, and entitled "METHOD AND APPARATUS FOR SURGICAL NAVIGATION"; U.S. Pat. No. 5,913,820, entitled "Position Location System," issued Jun. 22, 1999; and U.S. Pat. No. 5,592,939, entitled "Method and System for Navigating a Catheter Probe," issued Jan. 14, 1997; all of which are herein incorporated by reference. It will be understood that the navigation system 26 may also be or include any appropriate tracking system, including a STEALTHSTATION® TREON® or S7™ tracking systems having an optical localizer, that may be used as the optical localizer 88, and sold by Medtronic Navigation, Inc. of Louisville, Colorado. Other tracking systems include an acoustic, radiation, radar, etc. The tracking systems can be used according to generally known or described techniques in the above incorporated references. Details will not be included herein except when to clarify selected operation of the subject disclosure.

Wired or physical connections can interconnect the tracking systems, imaging device 80, etc. Alternatively, various portions, such as the instrument 68 may employ a wireless communications channel, such as that disclosed in U.S. Pat. No. 6,474,341, entitled "Surgical Communication Power System," issued Nov. 5, 2002, herein incorporated by reference, as opposed to being coupled directly to the processor system 102. Also, the tracking devices 62, 66, 170 can generate a field and/or signal that is sensed by the localizer(s) 88, 94.

Various portions of the navigation system 26, such as the instrument 68, and others as will be described in detail below, can be equipped with at least one, and generally multiple, of the tracking devices 66. The instrument can also include more than one type or modality of tracking device 66, such as an EM tracking device and/or an optical tracking device. The instrument 68 can include a graspable or manipulable portion at a proximal end and the tracking devices may be fixed near the manipulable portion of the instrument 68.

Additional representative or alternative localization and tracking system is set forth in U.S. Pat. No. 5,983,126, entitled "Catheter Location System and Method," issued Nov. 9, 1999, which is hereby incorporated by reference. The navigation system 26 may be a hybrid system that includes components from various tracking systems.

According to various embodiments, the navigation system 26 can be used to track the instrument 68 relative to the patient 30. The instrument 68 can be tracked with the tracking system, as discussed above. Image data of the patient 30, or an appropriate subject, can be used to assist the user 72 in guiding the instrument 68. The image data, however, is registered to the patient 30. The image data defines an image space that is registered to the patient space defined by the patient 30. The registration can be performed as discussed herein, automatically, manually, or combinations thereof.

Generally, registration allows a translation map to be generated of the physical location of the instrument 68 relative to the image space of the image data. The translation map allows the tracked position of the instrument 68 to be displayed on the display device 84 relative to the image data 108. A graphical representation **68*i*, also referred to as an icon, can be used to illustrate the location of the instrument 68 relative to the image data 108**.

Figure 2:
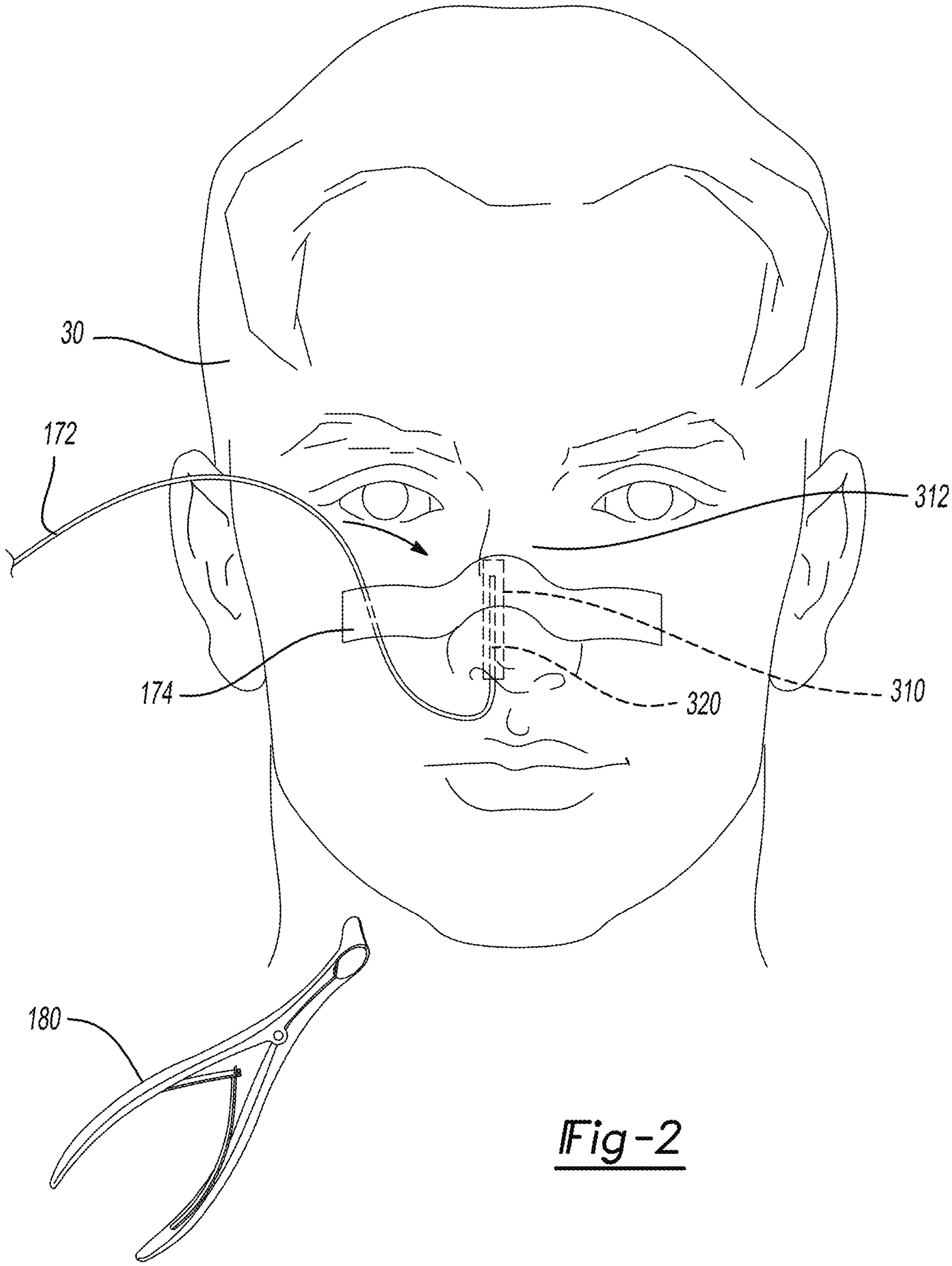
FIG. 2 is a front view of the endonasal dynamic tracking device of FIG. 1.
Figure 3A:
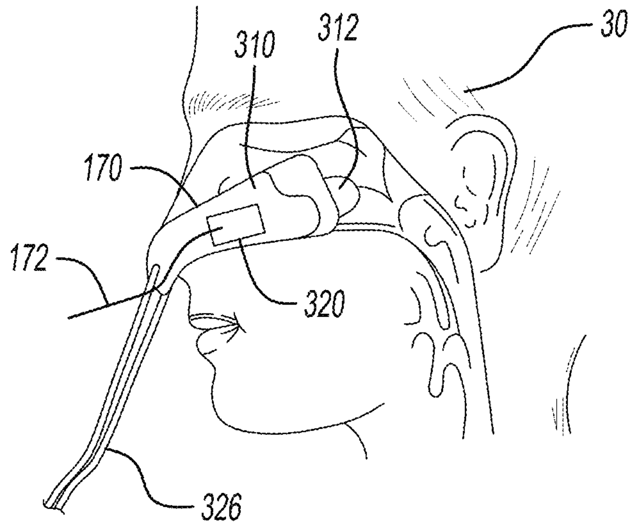
FIG. 3A is a first example of a patient tracking device within a body cavity.

Referring now to FIGS. 2 and 3A, the endonasal tracking device or patient tracking device 170 and cable 172 are illustrated disposed within a sensor housing 310 within a body cavity 312 of a patient 30. The patient tracking device 170 may be used as a dynamic reference frame (DRF) for various procedures such as but no limited to cranial procedures. The housing 310 may be formed of a conformable material such as a nasal tamponade (e.g. Merocel® nasal dressing by Medtronic). The cavity 312 may be a cranial cavity such as a nasal cavity having an irregular shape. The housing 310 may be conformable to the shape of the cavity 312. The housing 310 may transform its shape to be secured within the cavity 312 automatically or automatically in the presence of moisture such as water or bodily fluids. As will be described in more detail below, the size of the housing 310 may vary depending upon the particular body cavity 312 into which the patient tracking device 170 is located.

In FIGS. 2 and 3A-3C, the body cavity 312, in this example, is a nasal cavity such as the inferior nasal meatus. The body cavity 312 may be rigid. Other nasal cavities such as the middle and superior meatus may also receive a sensor housing 310 with appropriate changes to dimensions. Of course, the disclosure should not be limited to cranial, nasal cavities, oral cavities or surgical procedures. The sensor housing 310 is substantially, non-invasively fixed relative to the patient 30 and particularly fixed relative to the skull or cranium. A nasal speculum 180 may be used to insert the housing 310 and sensor 320 within the cavity 312. The housing 310 may be compressed during insertion. The housing 310 may expand into and conform to the cavity 312. The housing 310 may also be removed by way of a tool such as the nasal speculum. The housing 310 may have a first form at rest, a second form as it is being inserted and a third form within the body cavity.

The cable 172 is coupled to an electromagnetic sensor 320 that either generates an electromagnetic field or receives electromagnetic field from the EM localizer 94 and generates a current in the presence of the electromagnetic field. The cable 172 communicates signals to or from the sensor 320 depending on the mode of operation mentioned previously. The signals from the sensor 320 allow precise position of the sensor 320 to be determined relative to the components within the operating environment. One example of a suitable sensor 320 is an AxiEM sensor.

The housing 310 may optionally have a removing member or handle 326 coupled thereto. The handle 326 may be one or more strings or other flexible device that is used for removing the housing 310 from the subject 30. The handles 326 are particularly useful if the patient tracking device 170 is wireless.

Figure 3B:
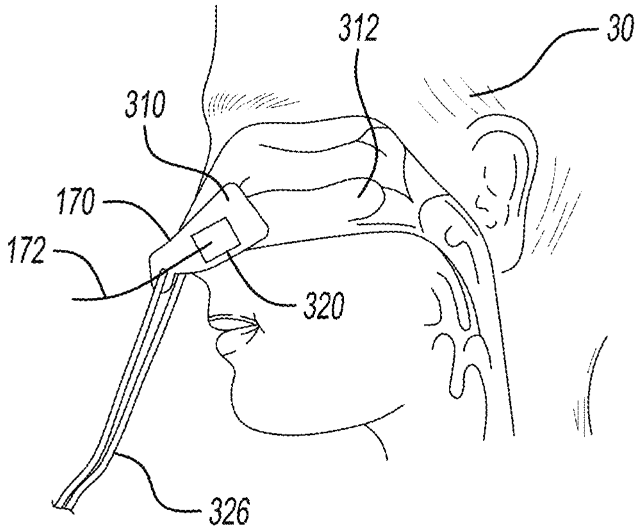
FIG. 3B is a second example of a patient tracking device within a body cavity.

Referring now to FIG. 3B, a different shape of housing 310 is set forth. In this example the housing 310 is shorter in length and has a dimension to fit within the entry to the nasal passage.

Figure 3C:
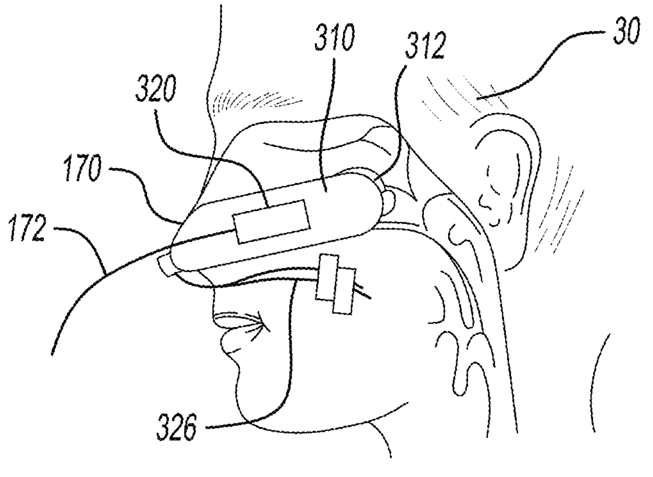
FIG. 3C is a third example of a patient tracking device within a body cavity.

Referring now to FIG. 3C, a larger housing 310 is illustrated having the sensor 320 disposed therein. In this example, the housing 310 is thicker and longer than those set forth in FIGS. 3A and 3B. As mentioned above, the shape of the housing 310 may vary depending upon the particular body cavity 312 as well as the size of the body cavity 312 and the size of the patient.

The housing 310 may automatically take the shape of the body cavity to substantially fix the sensor 320 in relation to the subject 30 in a non-invasive manner. The housing 310 may conform to an opening such as a nasal passage as it is being inserted. The sensor is fixed in shape and small enough to enter the desired opening. The housing 310 conforms to the cavity shape without the cavity having to conform to the housing. In this manner the housing 310 and sensor 320 are held in place during a procedure. The housing is non-invasively fixed to the subject.

Figure 4A:
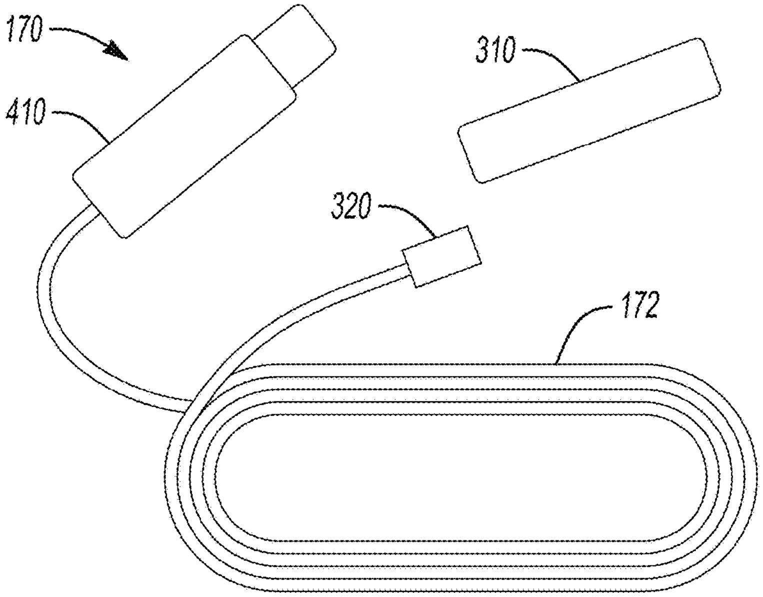
FIG. 4A is a partially exploded view of the patient tracking device.
Figure 4B:
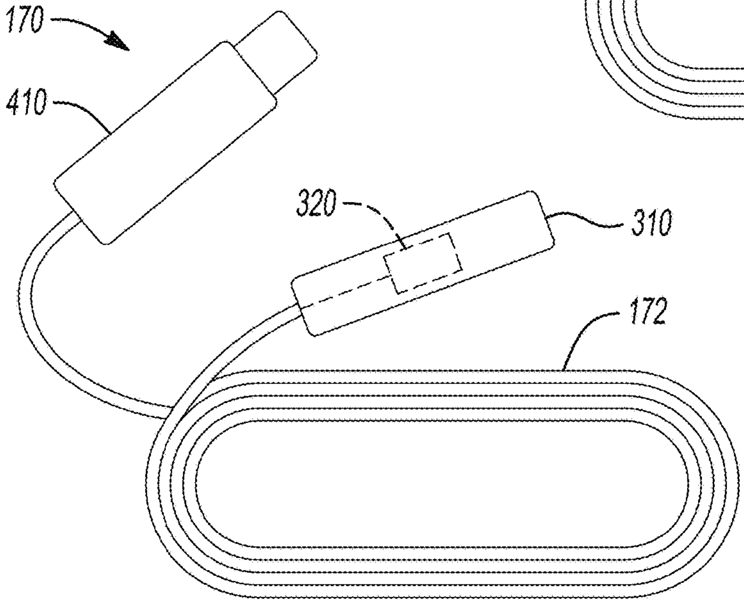
FIG. 4B is an assembled view of the patient tracking device.

Referring now to FIGS. 4A and 4B, a detailed view of one example of a patient tracking device 170 is set forth. In this example a connector 410 is used for connecting the patient tracking device 170 to the interface 110 set forth above. In FIG. 4A, the housing 310 is illustrated disassembled from the sensor 320. In FIG. 4B, the sensor 320 is illustrated within the housing 310. Details of the assembly of the housing 310 and the sensor 320 are set forth in greater detail below.

Figure 5:
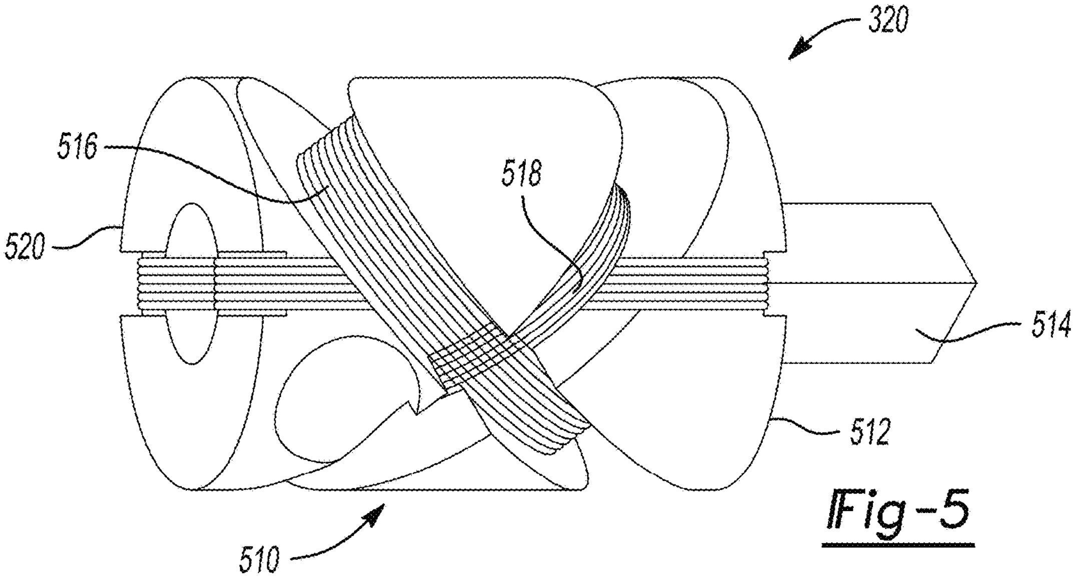
FIG. 5 is a perspective view of a sensor for the patient tracking device.

Referring now to FIG. 5, an exemplary electromagnetic EM coil configuration for the sensor is illustrated. An electromagnetic sensor bobbin 510 or multiple coil members may be positioned in a cavity of the patient tracking device 170. The sensor bobbin 510 includes a body 512 that is generally formed from material that is not conductive to allow the coils to operate and sense a position in a field. In addition, the body 512 may be manipulated by a manipulable portion or handle 514 extending from the body 512. In addition, the handle 514 may allow cable 172 to be interconnected to the body portion 512 into multiple coils. In this example, three coils 516, 518 and 520 are illustrated. However, fewer coils or more coils may be used in a sensor.

The first coil 516, the second coil 518 and third coil 520 are generally positioned at angles relative to one another. The angles may be any appropriate angle such as a generally orthogonal angle or other appropriate angle. The three coils 516, 518, 520 being positioned at angles relative to one another, allow for six degrees of freedom sensing including translation, angle, pitch, yaw, and rotation. Therefore, the position or movement of the patient tracking device 170 can be determined by sensing the electromagnetic field of the electromagnetic localizer 138.

Generally, the body 512 of the bobbin 510 and the exterior or the bodies of the patient tracking device 170 are formed of an appropriate material. For example, the material may be a non-metallic and non-conducting material such as an appropriate ceramic, plastic, and the like. The material may be selected from a material that will not interfere with either transmitting or receiving information regarding the magnetic field and not interfere with imaging of the subject 30.

Figure 6A:
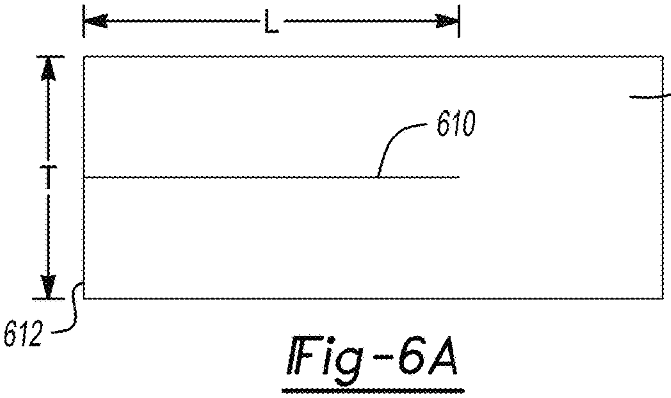
FIG. 6A is one example of a housing 310.

Referring now to FIG. 6A, the housing 310 is illustrated in further detail. The housing 310 may be formed of a flexible, resilient and conformable material such as nasal dressing (e.g. a nasal tamponade). The housing 410 is autoconformable and resilient in that the shape of the housing 410 automatically conforms to the shape of the cavity when inserted therein. In one example, the material is compressible and expandable when in contact with a fluid such as water. In either case, the housing material automatically fills and conforms to the cavity shape. The housing 310 is illustrated in its expanded form. The material of the housing 310 may also be sterile and disposable. In one example, the housing 310 is formed of hydroxylated polyvinyl acetate which is a compressed foam polymer. The material is conformable and compliant so that when the housing 310 is placed within a body cavity, the irregularities of the body cavity 312 are compensated for by the conforming housing 310. That is, the housing 310 may be retained in a fixed position within the body cavity 312 due to the conformable and compliant nature. The housing 310 is also resilient in that it may be compressed before or during placement within the body cavity 312 and expands after positioning within the body cavity 312 from a first configuration to a second configuration. As mentioned above, the material forming the housing 310 may be expandable when in contact with moisture or water. The housing 310 may include a longitudinally extending slot 610. In the present example the slot 610 is about half way between the thickness T and extends a length L less than the length of the housing 310.

Figure 6B:
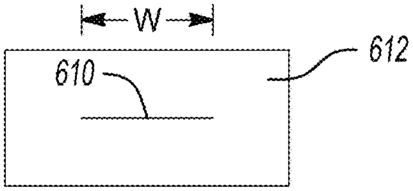
FIG. 6B is an end view of the housing of FIG. 6A.

Referring now to FIG. 6B, the slot 610 is illustrated in a lateral end side 612. The slot 610 extends a width W less than the width of the housing 310. The width W of the slot 610 is sized to receive the sensor 320 and cable 172 therein.

Figure 6C:
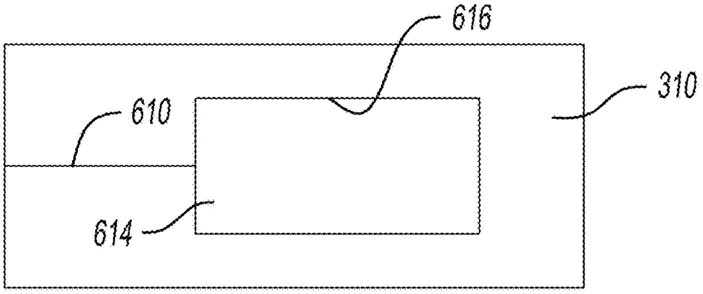
FIG. 6C is a side view of the housing having a cavity therein.

Referring now to FIG. 6C, the interior of the housing 310 may be pre-formed with a cavity 614 for receiving the sensor 320 therein. The cavity 614 may also be formed by placing the sensor 320 into the slot 610 within the housing 310. That is, because the material of the housing 310 is compressible, when the sensor 320 is inserted within the slot 610, the cavity 614 may be formed. The material directly adjacent to the cavity 614 may be more highly compressed than the material further from the cavity 614.

In a set of patient tracking devices, the length, width and thickness of multiple devices may vary to allow a number of options depending on the patient and cavity characteristics.

A retainer may optionally be used to secure the sensor within the cavity 614. In this example, the retainer may be an adhesive 616 that is disposed on at least some of the surfaces of the cavity 614. In this manner, when the sensor 320 is disposed within the cavity 614, the sensor 320 remains engaged with the housing 310. In one example, a drop or two of an adhesive material may be communicated through the slot 610 in to the cavity 614 prior to the insertion of the sensor 320 within the cavity 614. Ultimately, the adhesive 616 is forced toward the surfaces of the cavity 614. The types of retainers may be flexible and conformable to allow the patient tracker to conform to the cavity.

Figure 6D:
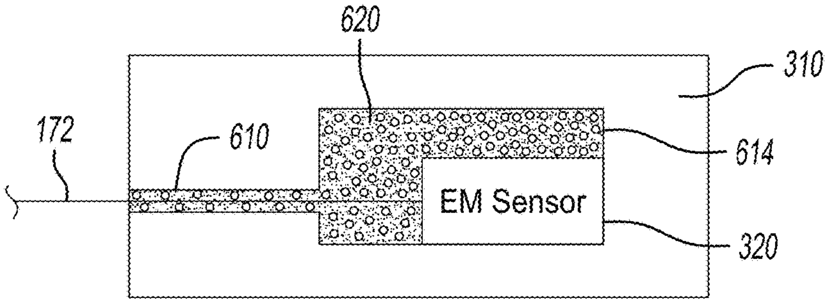
FIG. 6D is a cross-sectional view of a housing having a cavity that is only partially filled with a sensor.

Referring now to FIG. 6D, the sensor 320 may not completely fill the cavity 614. A biocompatible material 620 may be injected into the unfilled portion of the cavity 614 to securely lodge the electromagnetic sensor 320 and the cable 172 therein. A suitable biocompatible material is polylactic acid.

Figure 7A:
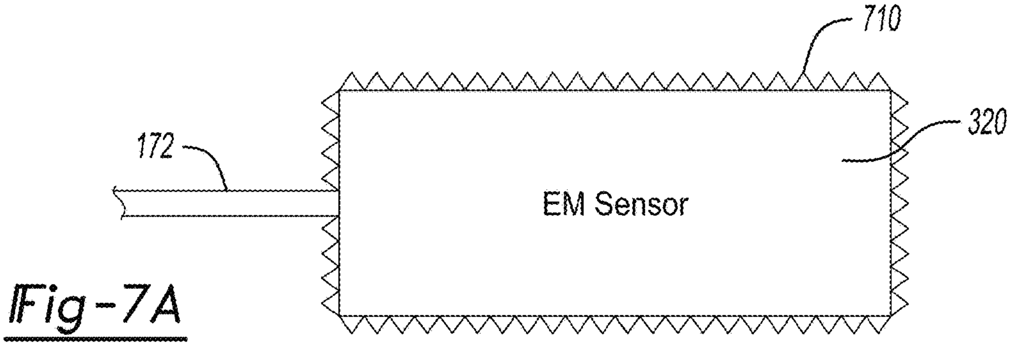
FIG. 7A is a side view of an electromagnetic sensor with a cable 172.

Referring now to FIG. 7A, the electromagnetic sensor 320 is illustrated with a cable 172 thereon. Adhesive 710 may be applied to the outer surface of the sensor 320 so that upon insertion within the cavity 614 of FIG. 6B the sensor is maintained therein.

Figure 7B:
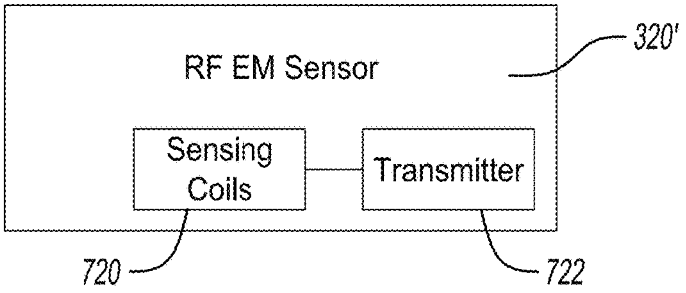
FIG. 7B is a block diagrammatic view of an wireless EM sensor.

Referring now to FIG. 7B, a wireless electromagnetic sensor 320' may also be provided. In this example, the wireless EM sensor may be formed with sensing coils 720 as described above. However, a wireless communication may be formed with the interface using a transmitter 722. Thus, the wireless EM sensor 320' may be fully enclosed within the housing 310 and thus no wire or cable 172, such as that illustrated above, is required for communication with the interface 110.

Referring now to FIG. 8A, one example of an assembled patient tracking device 170 is set forth. The handles 326 which are optional in all of the FIGS., are illustrated. The handles 326 may be drawstrings that are embedded within the material of the housing 310. The handles 326 may be adhesively bonded within the housing 310 so that they may be used to remove the patient tracking device 170 when the patient tracking device is no longer needed. In this example, the sensor 320 is held within the housing 310 by adhesive 810 disposed at the interface between the sensor housing 310 and cable 172.

Referring now to FIG. 8B, the same reference numerals are used as those set forth in FIG. 8A. However, in this example a clip or fastener 820 is used for securing the cable 172 to the housing and thus the sensor 320 is secured within the cavity of the housing 310.

Figure 17:
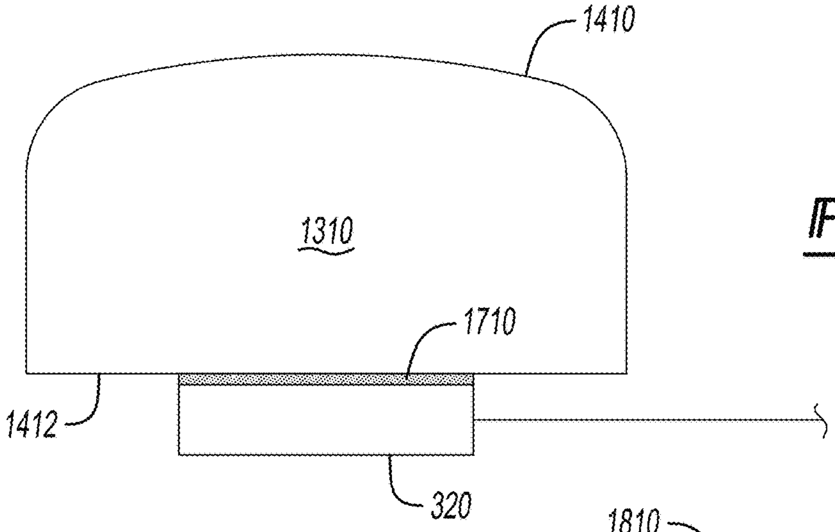
FIG. 17 is a side view of the sensor housing with the sensor mounted thereto.

Referring now to FIG. 17, another type of clip or fastener 822 is illustrated. In this example the clip or fastener 822 extends from an upper surface 824 to a lower surface 826. The clip or fastener 822 has arms 828 that are directly adjacent to the respective surfaces 824 and 826 and provide a clamping force to secure the cable 172 therein. As mentioned above, the clips or fasteners may be flexible so that they allow the housing to be inserted into the body cavity.

In FIGS. 8A and 8B, the clips or fasteners 820, 822 may be formed of a dielectric material so that they do not interfere with the electromagnetic fields sensed or generated by the electromagnetic sensor 320.

The sensor 320 may also be secured by heat sealing or by overmolding the sensor 320 within the material of the housing 310 during the forming of the housing 310. The handles 326 may also form a drawstring that are used to secure the cable 172 to the housing or close the slot so that the sensor 320 is retained within the housing 310.

The handles 326 may not be required should the housing 310 be removed with a separate instrument. The housing 310 may also be removed by pulling on the cable 172. In such a case, the retainer such as the adhesive 810, or the clips or fasteners 820, 822 are stronger than the force required to pull the housing 310 from the body cavity of the subject 30.

Referring now to FIG. 9A, the wireless EM sensor 320' is illustrated in further detail. In this example, the handles 326 may be required to allow removal of the housing 310 from the body cavity of the subject. In FIGS. 9A-9C the slot 610 illustrated above in FIGS. 6A-6B are illustrated. In FIGS. 8A-8C the slot has been filled by the cable 172. However, in the case of the RF EM sensor 320' no wire is required. Thus, when the sensor 320' is inserted within the cavity 614, the slot 610 may be sealed with adhesive 910. FIGS. 9B and 9C may use clips or fasteners 820, 822 to enclose the sensor 320' within the cavity of the housing 310.

Figure 10:
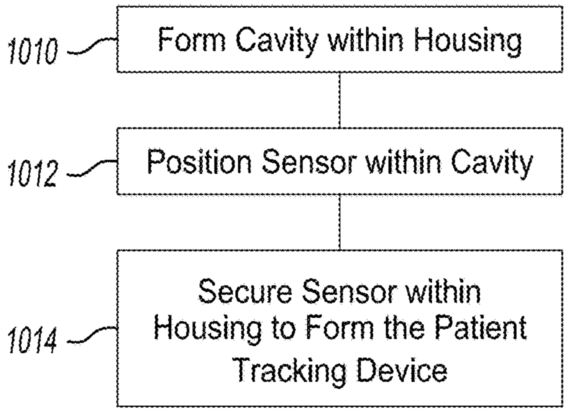
FIG. 10 is a flowchart of a method for forming the patient tracking device.

Referring now to FIG. 10, a method for forming the patient tracking device 170 is set forth. In block 1010, a cavity is formed within the housing. As mentioned above, the housing may be conformable and the cavity may be pre-formed or automatically formed as the sensor 320 is inserted within the housing 310. In block 1012, the sensor 320 is positioned within the cavity 614. The sensor may be positioned within the cavity 614 by insertion through the slot 610 illustrated above. In block 1014, the sensor is secured within the housing using a retainer such as but not limited to adhesive, clips, fasteners, overmolding, or heat staking, et cetera.

Figure 11:
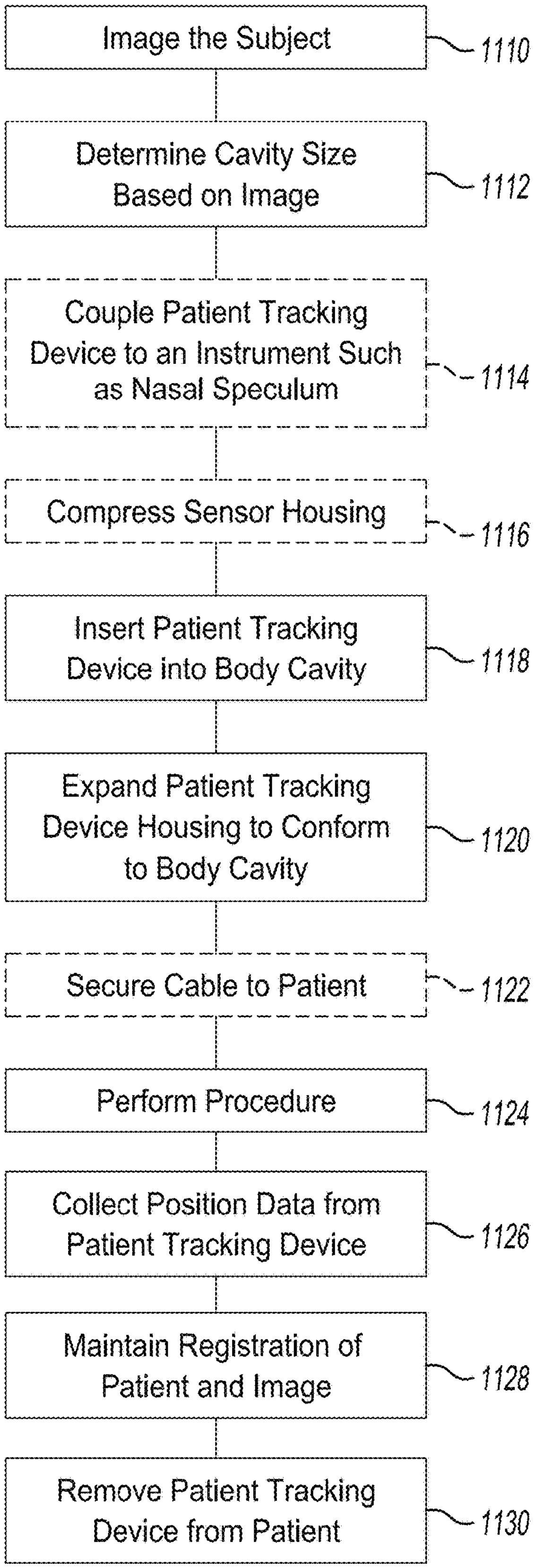
FIG. 11 is a method for using the patient tracking device.

Referring now to FIG. 11, the use of the patient tracking device for a procedure is set forth. In block 1110, the subject is imaged. During the imaging of the subject, the body cavity within which the patient tracking device is to be secured during the procedure may be determined. In block 1112, the cavity size is determined for the body cavity based upon the image determined in block 1110.

An optional block 1114 may also be performed. In block 1114, the patient tracking device may be coupled to an instrument such as a nasal speculum for insertion. However, an instrument such as a nasal speculum may not be required if the patient tracking device is in a compressed state before insertion. The use and type of the instrument in block 1114 depends upon the particular body cavity and the type of sensor and the material of the housing.

In block 1116, the sensor housing may be compressed manually or using an instrument. This is an optional block since the sensor housing may also be compressed prior to insertion or during insertion by the rigid body cavity walls. In block 1118 the patient tracking device is inserted into the body cavity. In block 1120, the patient tracking device housing is automatically expanded to conform, nest, deform or otherwise be fixed into to the body cavity. That is, the housing 310 is changed from a first configuration or shape into a second configuration or shape. In block 1122, the cable is secured to the patient using an adhesive or tape. In block 1124, the procedure is performed. During the procedure, block 1126 collects data from the patient position sensor (DRF) and adjusts the navigation location in block 1128. The navigation location in block 1128 maintains the registration of the patient and the image in response to any movement of the patient. The correlation of the patient and the images is maintained.

In block 1130, the patient tracking device may be removed from the patient and disposed of. The conforming housing may allow the patient tracking device to easily be removed by handle, cable or using an instrument. In this manner, the insertion and the removal of the patient tracking device is non-invasive to the subject.

The sensor assembly set forth herein may be used as a dynamic reference frame and is particularly suited for body cavity insertion such as a nasal cavity during cranial procedures. The housing 310 may be compressed manually or by tool (or not at all). The housing material conforms to the rigid body cavity without deformation of the body cavity. The sensor assembly can be used interopertively without incisions or fixing to the subject with screws or other invasive methods.

Figure 12:
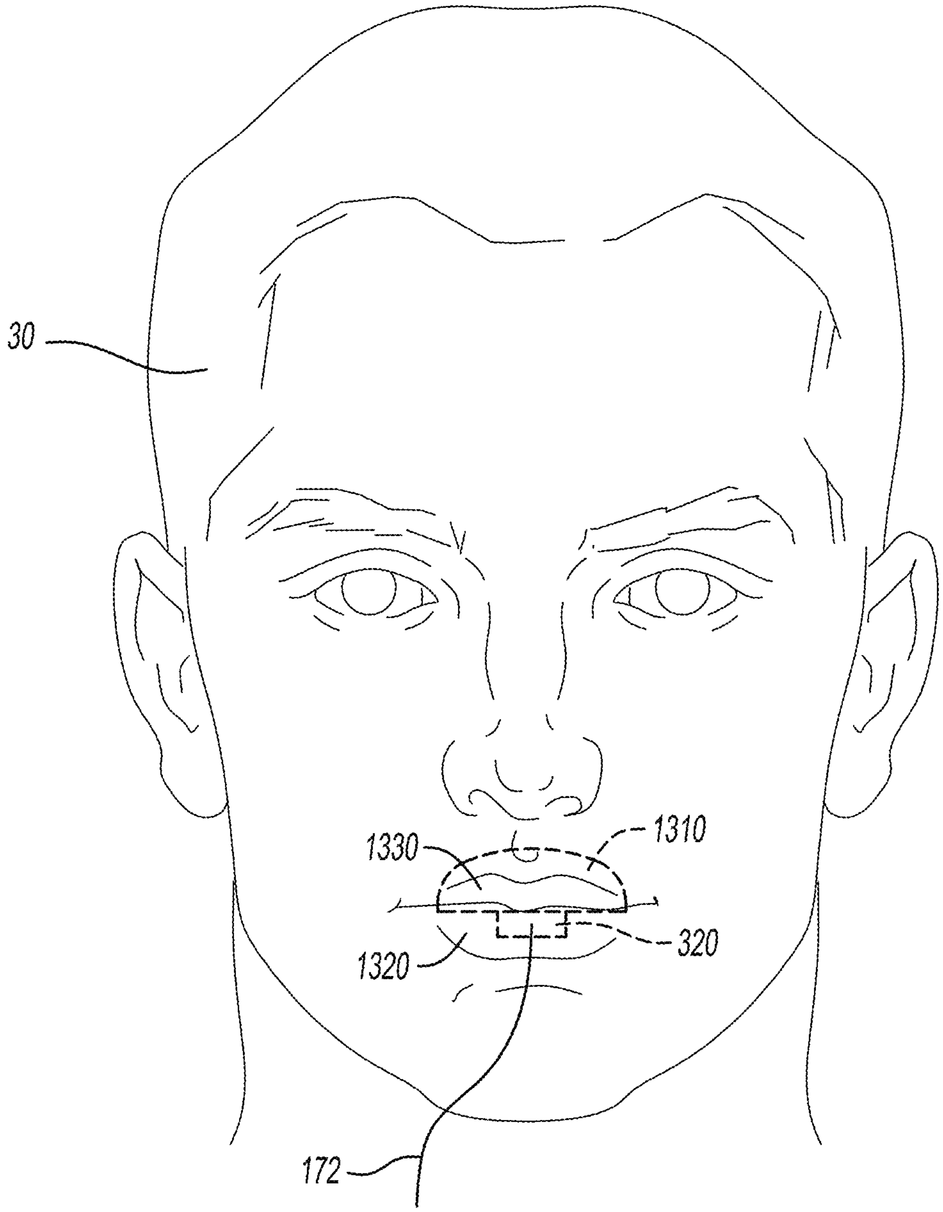
FIG. 12 is a cutaway front view of the patient having an oral sensor housing
Figure 13:
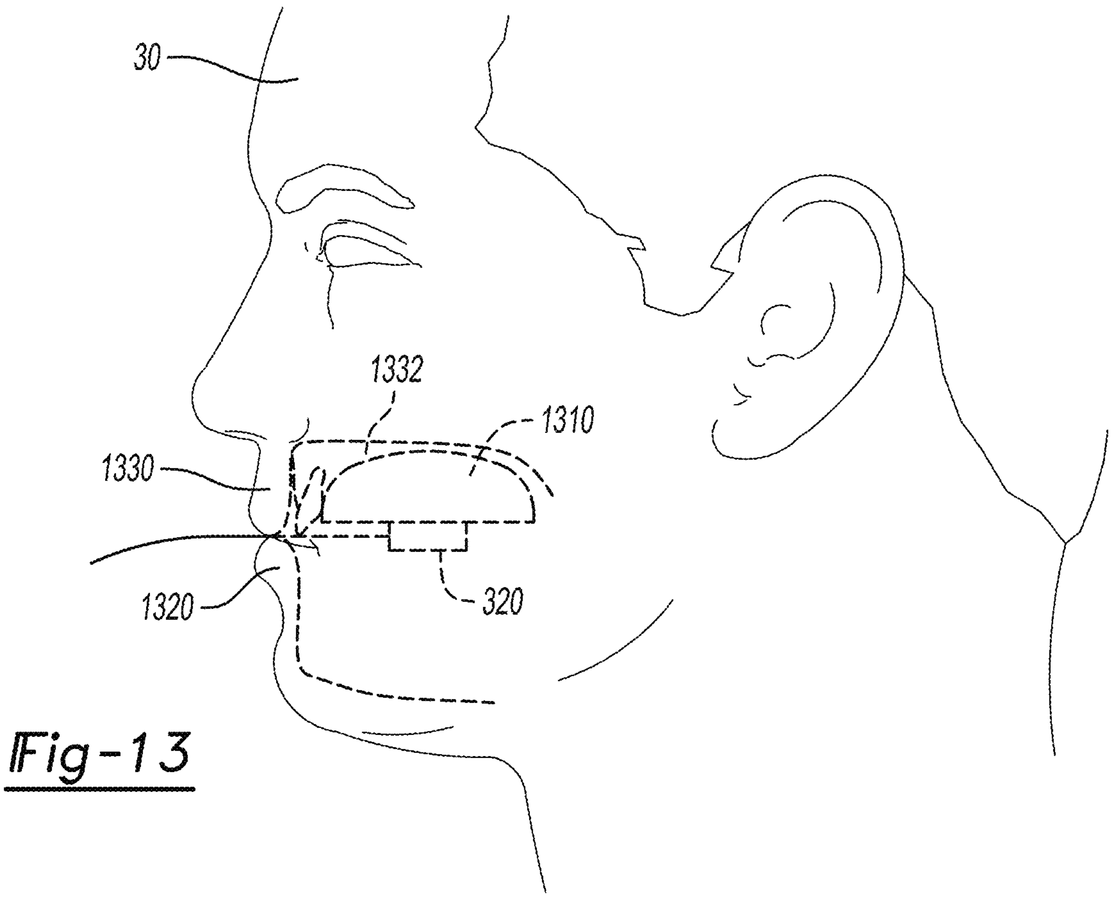
FIG. 13 is a cutaway side view of the patient having an oral sensor housing.

Referring now to FIGS. 12 and 13, a sensor housing 1310 having an electromagnetic sensor 320 coupled thereto may be mounted within an oral cavity 1320 of patient 30. The housing 1310 may be formed in various ways including three-dimensional printing. One suitable biocompatible material for housing 1310 is polylactic acid. The housing 310 may be affixed to the palate 1330 or teeth 1332 or both. The sensor housing 1310 and electromagnetic sensor 320 may be used in the system of claim 1. The use of the oral sensor housing 1310 is suitable for cranial procedures when access to or through the nasal passages are required.

Figure 14:
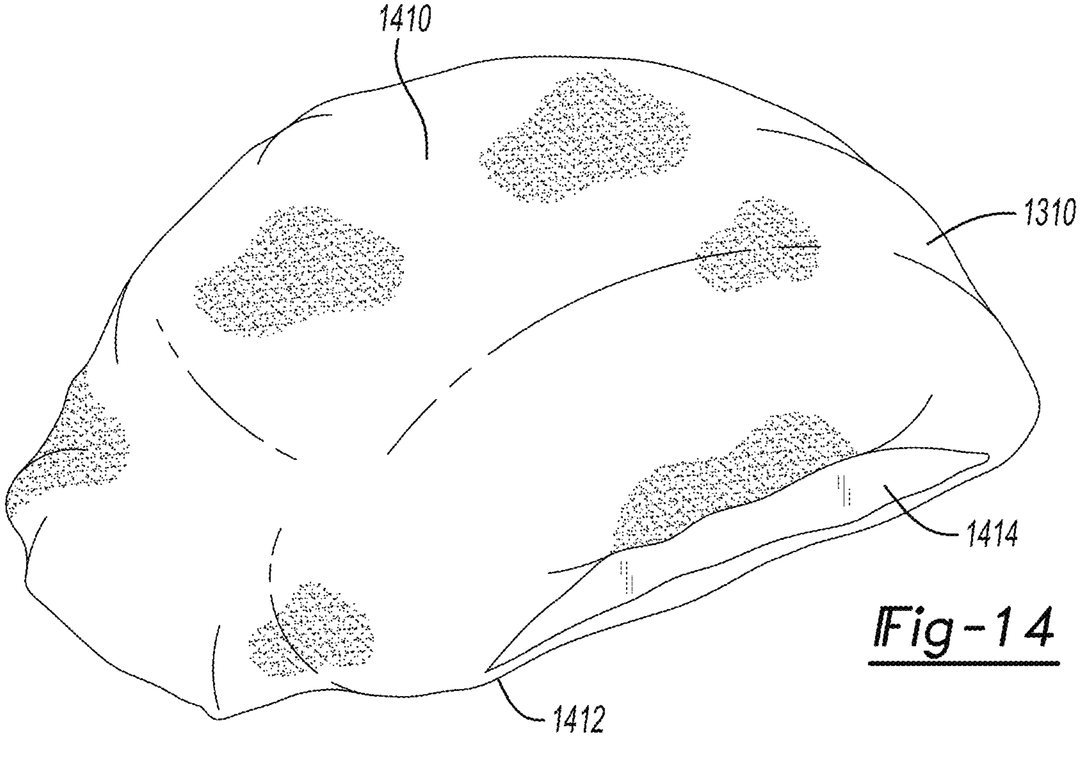
FIG. 14 is a top perspective view of the sensor housing.
Figure 15:
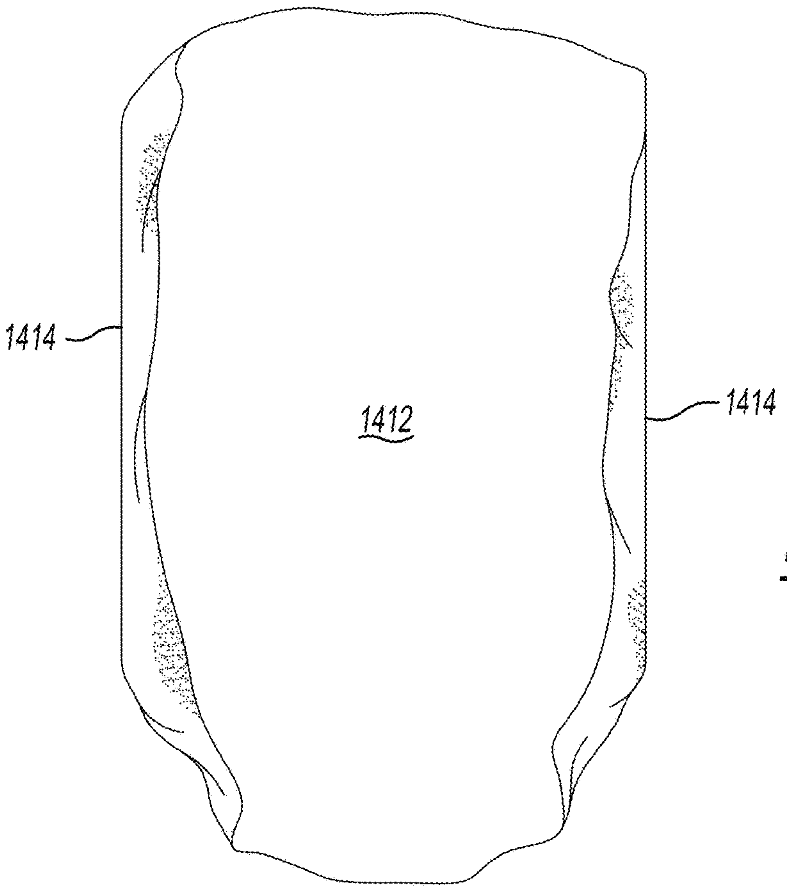
FIG. 15 is a bottom view of the sensor housing.

Referring now to FIGS. 14 and 15, the sensor housing 1310 is illustrated in further detail. The sensor housing 1310 includes a first surface 1410 and a second surface 1412. The first surface 1410 is based upon the surface of the palate 1330. As will be further described below, a computed tomography (CT) image may be formed of the oral cavity of the patient 30. The housing 1310 may be formed by three-dimensional printing or the like and may be based on the CT image in order for the first surface to rest with the palate. The housing may also be molded from a negative of the palate surface as is described below. The second surface 1412 may be of an arbitrary shape and include a planer portion as will be illustrated below. A third and fourth surface 1414 may be shaped to conform to the profile of the teeth so that ultimately an adhesive may be used on the surfaces 1414 to adhesively join the teeth and the housing 1310.

The surface 1410 may be formed especially for an individual patient. Also, the surface 1410 may be formed by a general patient size to be relatively close to various types of patients. That is, a set of various size housings 1310 may be formed for a doctor to select from. The material of the housing may be flexible to allow a fit within the oral cavity. For example, a large, medium or small adult and a large, medium or small child may all be sized differently. The surface 1410 may be rounded generally to conform to the size. The surfaces 1414 may be used to adhesively join one of the selected housings from the set of housings to the patient 30.

Figure 16:
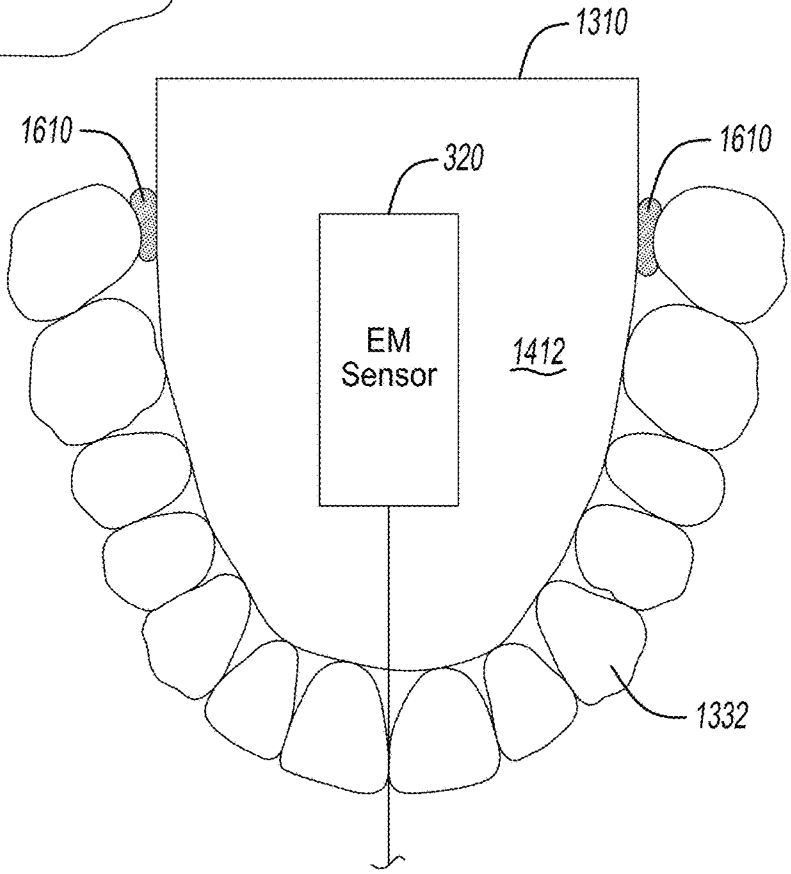
FIG. 16 is a view of the sensor housing mounted within a palate of a patient.

Referring now to FIG. 16, a plurality of teeth 1332 are illustrated. The teeth 1332 may be adhesively coupled to the sensor housing 1310 by an adhesive 1610. In addition to an adhesive on the teeth 1332, adhesive 1610 on the palate or merely saliva from the patient may be used to secure the sensor housing 1310 within the oral cavity 1320 of the patient 30.

Referring now to FIG. 17, a side view of an assembled sensor housing 1310 is set forth. The sensor housing 1310 is set forth in great detail in FIGS. 4A, 4B and 5. In all instances the electromagnetic sensor 320 may be replaced with the wireless electromagnetic sensor 320' illustrated in FIG. 7B. The sensor 320 illustrated in FIG. 17, is secured to the surface 1412 with adhesive 1710.

Figure 18:
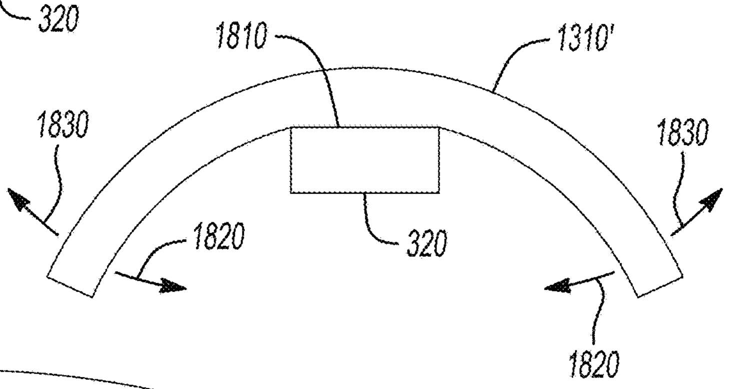
FIG. 18 is a view of a first alternate method for mounting a sensor housing.

Referring now to FIG. 18, the sensor 310 may be coupled to a planer surface 1810 of the sensor housing 1310'. In this example, the shape of the housing 1310' is a convex shape and the sensor 310 is coupled to the planer surface 1810. For this example, adhesive may also be used to affix the housing 1310' to the teeth 1332.

Figure 19:
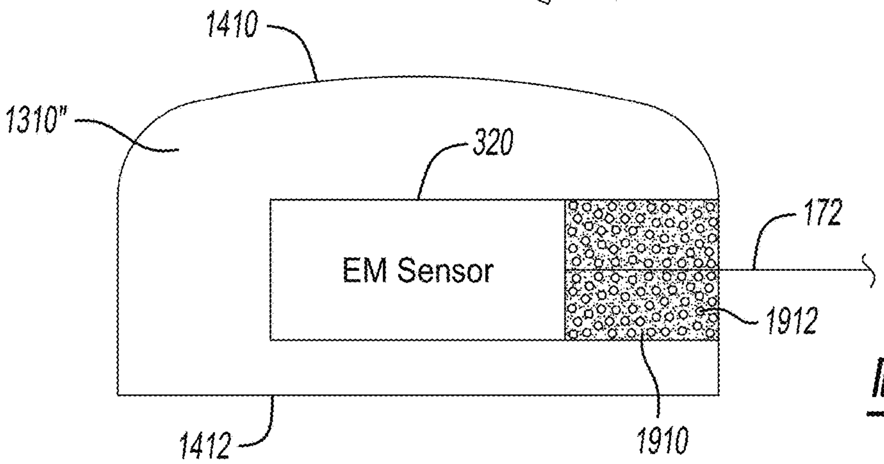
FIG. 19 is a cutaway view of a sensor housing having a sensor mounted therein.

Referring now to FIG. 19, the sensor 310 may also be formed within a cavity 1910 of the sensor housing 1310". The cavity 1910 may be sized to receive the sensor 310 therein as well as allowing the wire 172 to extend therefrom. A biocompatible material 1912 may be used to retain the electromagnetic sensor 310 within the cavity 1910. The biocompatible material 1912 may be an adhesive or may be formed from the same material as the housing 1310".

Figure 20:
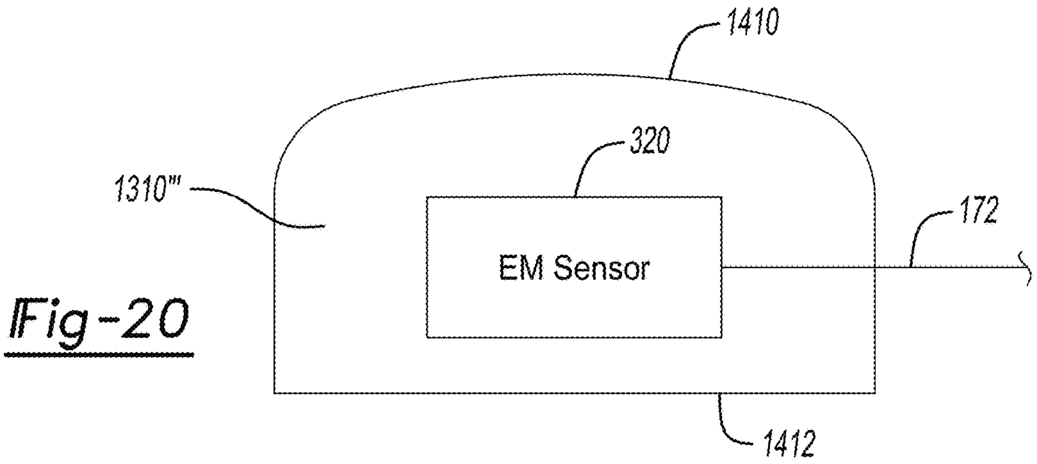
FIG. 20 is a side view of a sensor having a sensor over-molded therein.

Referring now FIG. 20, the electromagnetic sensor 310 may be over-molded within the material of the housing 1310'". The first surface 1410 and the second surface 1412 may be formed in a similar manner.

Figure 21:
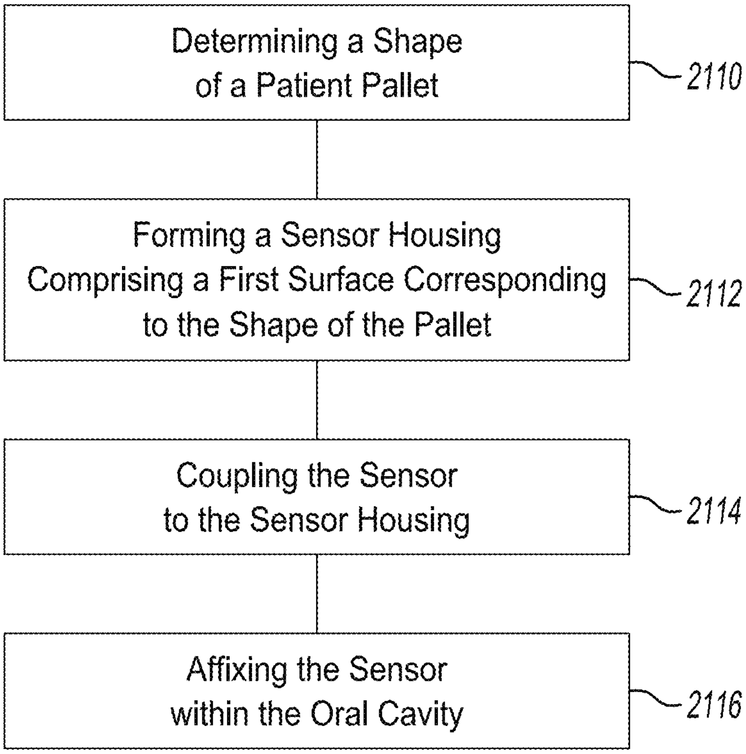
FIG. 21 is a flowchart of a method for forming the sensor.

Referring now to FIG. 21, a method for forming the palate housing is set forth. In step 2110 a shape of the patient's palate is determined. The shape of the patient's palate may be formed by a noninvasive method such as using a CT image. In step 2112, the CT image may be used to form the sensor housing and in particular the first surface of the sensor housing to correspond to the shape of the palate. An exact mirror image of the palate surface of the patient may be obtained using the CT image. However, a completely exact match is not necessary. The sensor housing may be three-dimensionally printed based on the CT scan. Alternatively, a negative print of the palate may be obtained. The sensor housing may use the negative print as a surface of a mold. That is the housing is molded based on the negative print. The sensor housing may then be adhesively coupled to the sensor using adhesive heat staking or the like. As mentioned above, over-molding the sensor may also be over-molded within the material of the sensor. The sensor may be affixed within the oral cavity to perform a procedure as described above.

In all cases, the material of the sensor housing may have a slight flex so that, when inserted into the palate of a patient the housing flexes and provides force against the teeth, the palate or both for retaining or helping retain the housing within the oral cavity. For example, in FIG. 18 arrows 1820 represent inward flexing for insertion and arrows 1830 illustrate the direction of flex after release into the patient.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A patient tracking device for insertion into an oral cavity comprising:

an electromagnetic sensor; and a flexible sensor housing having a first convex surface sized to engage a palate within the oral cavity, and a second surface and a third surface each sized to engage against spaced apart teeth in the oral cavity, wherein the second surface and the third surface are configured to flex inward from a first position to a second position for insertion into the oral cavity and to return towards the first position after being released within the oral cavity, the flexible sensor housing configured to receive the electromagnetic sensor, wherein the electromagnetic sensor is coupled to the flexible sensor housing so as to be positioned within the oral cavity.

2. The patient tracking device of claim 1, wherein the flexible sensor housing defines a cavity that is configured to receive the electromagnetic sensor.

3. The patient tracking device of claim 2, wherein a biocompatible material is received within the cavity to retain the electromagnetic sensor within the cavity of the flexible sensor housing.

4. The patient tracking device of claim 1, wherein the flexible sensor housing is over-molded with the electromagnetic sensor to retain the electromagnetic sensor within the flexible sensor housing.

5. The patient tracking device of claim 4, wherein the flexible sensor housing further includes a fourth surface opposite the first convex surface, wherein the fourth surface has at least a planar portion.

6. The patient tracking device of claim 1, wherein the flexible sensor housing further includes a fourth surface opposite the first convex surface, wherein the fourth surface has at least a planar portion.

7. The patient tracking device of claim 6, wherein the electromagnetic sensor is coupled to the planar portion of the fourth surface.

8. The patient tracking device of claim 1, wherein the first convex surface is shaped to correspond to the palate within the oral cavity.

9. The patient tracking device of claim 8, wherein the flexible sensor housing is 3-dimensionally printed and formed of polylactic acid.

10. The patient tracking device of claim 1, wherein the the second surface and the third surface flex and provide force against the spaced apart teeth within the oral cavity to assist in retaining the flexible sensor housing within the oral cavity.

11. The patient tracking device of claim 1, wherein the electromagnetic sensor is a wireless electromagnetic sensor.

12. The patient tracking device of claim 1, further comprising a first adhesive portion at the second surface and a second adhesive portion at the third surface to adhere the flexible sensor housing to the spaced apart teeth within the oral cavity.

13. The patient tracking device of claim 1, wherein the second and third surfaces are shaped to conform to a profile of the spaced apart teeth in the oral cavity.

14. A patient tracking device for insertion into an oral cavity of a patient comprising:

an electromagnetic sensor; and a flexible sensor housing having a first 3-dimensional surface configured to correspond to a palate within the oral cavity and an opposed second surface, the flexible sensor housing defining a cavity configured to receive the electromagnetic sensor and disposed within the flexible sensor housing between the first and second surfaces, wherein the electromagnetic sensor is sized to fit within the cavity and be carried by the flexible sensor housing, and wherein the flexible sensor housing includes a third surface and a fourth surface configured to flex inward from a first position to a second position for insertion into the oral cavity and to return towards the first position after being released within the oral cavity.

15. The patient tracking device of claim 14, wherein a biocompatible material is received within the cavity to retain the electromagnetic sensor within the cavity of the flexible sensor housing.

16. The patient tracking device of claim 14, wherein the fourth surface is opposed to the third surface, and wherein the third surface and the fourth surface are sized to engage against spaced apart teeth in the oral cavity.

17. The patient tracking device of claim 16, wherein the third and fourth surfaces are shaped to conform to a profile of the spaced apart teeth in the oral cavity.

18. The patient tracking device of claim 14, wherein the flexible sensor housing is molded from a negative print in response to an image scan of the oral cavity of the patient.

19. The patient tracking device of claim 14, wherein the second surface is planar.

* * * * *